(12) United States Patent
Lin (10) Patent No.: US 11,583,850 B2
(45) Date of Patent: Feb. 21, 2023

(54) TEST STRIP AND METHOD FOR MANUFACTURATING TEST STRIPS

(71) Applicant: MICROLIFE CORPORATION, Taipei (TW)

(72) Inventor: Wen-Guay Lin, Taipei (TW)

(73) Assignee: MICROLIFE CORPORATION, Taipei (TW)

( * ) Notice: Subject to any disclaimer, the term of this patent is extended or adjusted under 35 U.S.C. 154(b) by 348 days.

(21) Appl. No.: 17/032,078

(22) Filed: Sep. 25, 2020

(65) Prior Publication Data
US 2021/0086177 A1    Mar. 25, 2021

(30) Foreign Application Priority Data

Sep. 25, 2019 (TW) ................................ 108134544
Oct. 9, 2019 (TW) ................................ 108136543

(51) Int. Cl.
*B01L 3/00* (2006.01)

(52) U.S. Cl.
CPC ......... *B01L 3/5023* (2013.01); *B01L 2200/12* (2013.01); *B01L 2200/143* (2013.01); *B01L 2300/02* (2013.01); *B01L 2300/0825* (2013.01)

(58) Field of Classification Search
CPC ............... B01L 3/5023; B01L 2200/12; B01L 2200/143; B01L 2300/02; B01L 2300/0825; G01N 21/8483; G01N 33/526; G01N 33/66; G01N 21/4738; C12Q 1/54
See application file for complete search history.

(56) References Cited

U.S. PATENT DOCUMENTS

| | | | |
|---|---|---|---|
| 6,858,401 B2 | 2/2005 | Phillips et al. | |
| 2007/0259431 A1* | 11/2007 | Charlton | G01N 21/8483 73/61.41 |
| 2020/0371020 A1* | 11/2020 | Chai | G01N 21/78 |

FOREIGN PATENT DOCUMENTS

| | | | | |
|---|---|---|---|---|
| CN | 1099035 C | | 1/2003 | |
| WO | WO-2019171731 A1 * | | 9/2019 | C07D 519/00 |

* cited by examiner

*Primary Examiner* — Dennis White
(74) *Attorney, Agent, or Firm* — Juan Carlos A. Marquez; Marquez IP Law Office, PLLC (57) ABSTRACT

The application discloses a test strip and a method for manufacturing the test strip. The test strip comprises a base layer; an intermediate layer overlaid on the base layer; a blood retaining layer comprising a slit and a blood retaining region fluidly commuted with the slit and overlaid on the intermediate layer; an upper layer overlaid on the blood retaining layer; a reagent disposed on a surface of the intermediate layer and exposed to the slit, wherein there are an expectedly predetermined depth and a measured depth from an interface between the slit and the upper layer to an upper surface of the intermediate layer; and a classification mark representing a compensation factor and disposed on an upper surface of the upper layer or a lower surface of the base layer; wherein the compensation factor is the product of a difference between the predetermined depth and the measured depth and a reciprocal of the predetermined depth.

20 Claims, 9 Drawing Sheets

FIG. 9

TEST STRIP AND METHOD FOR MANUFACTURATING TEST STRIPS

CROSS-REFERENCE TO RELATED APPLICATION

This application claims priority from Taiwan Patent Application Nos. 108134544 filed on Sep. 25, 2019 and 108136543 filed on Oct. 29, 2019, which are hereby incorporated herein by reference in its entirety.

BACKGROUND OF THE INVENTION

1. Field of the Invention

The invention relates to a test strip capable of correcting errors caused from the variation in the actual depths of the slit of a blood retaining layer within the test strip and a method for manufacturing the test strip.

2. Description of Related Art

Diabetes is a clinical syndrome caused by various factors such as absolute or relative lack of insulin in the body, abnormal secretion time, and disorder or resistance of insulin acting bodies. If diabetes is not well controlled, it will cause some acute complications, such as hypoglycemia, ketoacidosis, and non-ketone hyperosmolar coma. Serious long-term complications include cardiovascular disease, chronic renal failure, retinopathy, neuropathy, microvascular disease, etc.

For diabetic patients, it is very important to monitor blood glucose from time to time. The primary goal of managing diabetes is to maintain a normal blood glucose value. If the patient can pay more attention to blood glucose control, he will be effectively prevented from the above complications. At present, most of the blood glucose meters used at home on the market utilize whole blood glucose tests. For example, the blood glucose concentration is determined by electrochemical or photochemical methods after the patient's blood is collected with a blood sampling needle and test paper.

Figure 1:
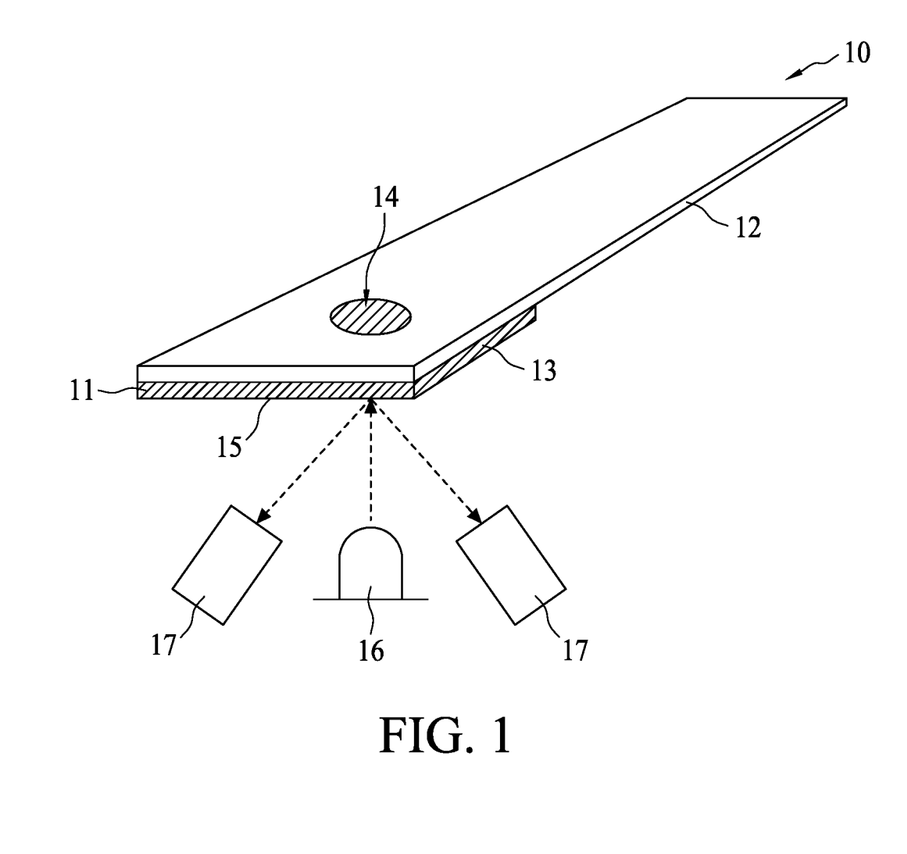
FIG. 1 is a schematic diagram illustrating a conventional test strip and an optical inspection used thereof.

China Patent No. CN1099035C discloses a test strip for detecting blood glucose, such as the test strip 10 is shown in FIG. 1. A reagent pad 11 with a hydrophilic group is fixed on a surface of a plastic carrier 12 by an adhesive 13, and the plastic carrier 12 has a hole 14 within the part which is adhered to the reagent pad 11. The blood sample is dripped from the hole 14 into the pore within the reagent pad 11 and reaches a testing surface 15. The reagent in the test pad 11 can chemically react with blood glucose. A light-emitting diode 16 projects light on the testing surface 15, and a light detector 17 receives light diffusely reflected from the testing surface 15. According to the change in the reflectance or reflective ratio observed on the testing surface 15, the blood glucose value in the blood can be obtained. In order to make the change in reflectance be more accurately representative the blood glucose value, it is even necessary to use different wavelengths of light to complete multiple calibrations before testing. Since the blood glucose value is obtained from the change in reflectance or reflective ratio for the test strip 10, not only are the calibrations complicated, but also the diffusely reflected light to be received is easily affected by ambient light.

Figure 2A:
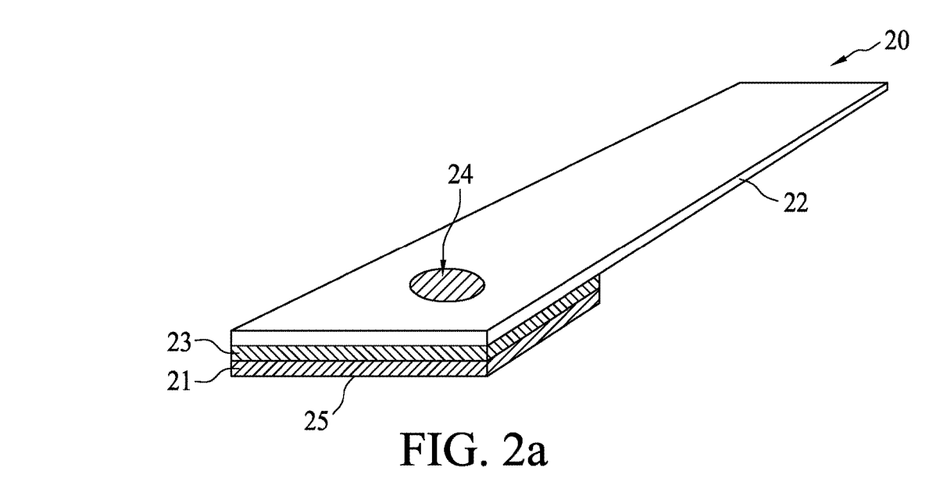
FIG. 2a is a perspective schematic diagram illustrating a conventional test strip.
Figure 2B:
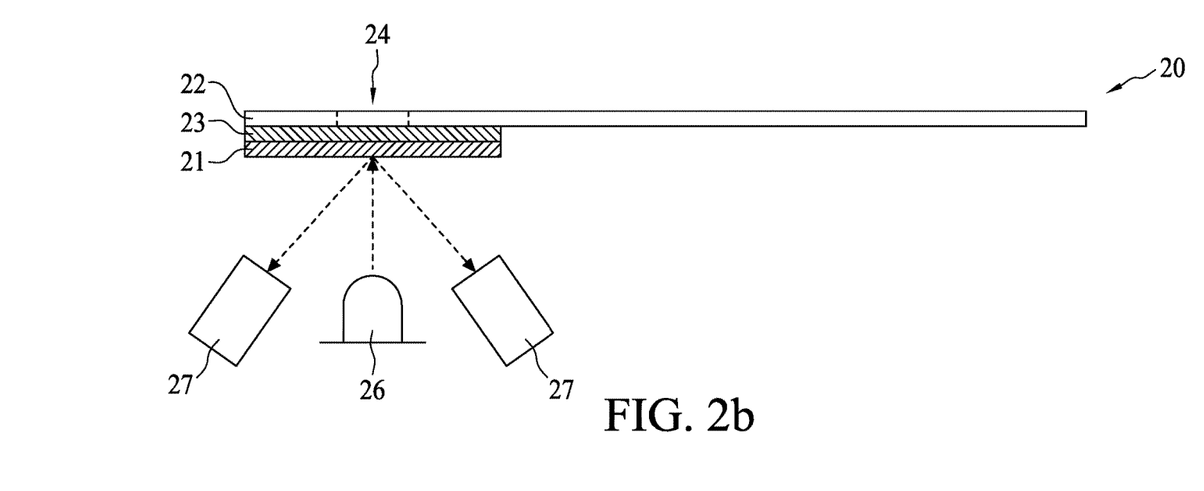
FIG. 2b is a schematic diagram illustrating a conventional reflective optical inspection.

Furthermore, U.S. Pat. No. 6,858,401 discloses a test strip for detecting blood glucose, and such a test strip 20 is shown as a perspective view in FIG. 2a. A reagent pad 21 with a hydrophilic group is fixed on a surface of a plastic carrier 22 by an adhesive 23. The plastic carrier 22 has a hole 24 in the part which is adhered to the reagent pad 21. The blood sample is dripped from the hole 24 into the pore within the reagent pad 21 and reaches a test surface 25. The reagent in the reagent pad 21 can chemically react with blood glucose. As shown in FIG. 2b, in the reflective optical detection method, a light emitting diode 26 projects light on the testing surface 25, and a light detector 27 receives light diffusely reflected from the testing surface 25. According to the change in reflectance or reflective ratio observed on the testing surface 25, the blood glucose value in the blood can be obtained. Because the thickness and surface roughness of the adhesive 23 vary, the diffusely reflected light received by the photodetector 27 also varies accordingly. That is, the detected blood glucose value will lose accuracy due to the variation in the quality of the adhesive 23. In addition, the transmissive optical inspection method also has the same problems as described above, and it is impossible to control the thickness and surface roughness of the adhesive 23 to be uniform during the manufacturing process of the test strip. Therefore, it is difficult to commercialize the test strip 20 and mass-produce it.

In order to ensure the accuracy of blood glucose measurement, the present invention provides a test strip for measuring blood glucose which is adaptive to the test strip classification for automatic correction. Also, the present invention provides a manufacturing method of capable measuring the length of an actual optical path and labeling a classification mark on the test strip.

SUMMARY OF THE INVENTION

According to one aspect of the application, a test strip adaptive is provided to be adaptive to a test strip classification for automatic correction.

According to another aspect of the application, a method for manufacturing a test strip is provided to measure the length of an actual optical path and label a classification mark on the test strip.

Thus, in one embodiment, the present application provides a test strip. The test strip comprises: a base layer; an intermediate layer overlaid on the base layer; a blood retaining layer comprising a slit and a blood retaining region fluidly commuted with the slit and overlaid on the intermediate layer; an upper layer overlaid on the blood retaining layer; a reagent disposed on a surface of the intermediate layer and exposed in the slit, wherein there are a predetermined depth and a actual depth from an interface between the slit and the upper layer to an upper surface of the reagent; and a classification mark representing a correction factor and disposed on an upper surface of the upper layer or a lower surface of the base layer; wherein the correction factor is the product of a difference between the predetermined depth and the actual depth and a reciprocal of the predetermined depth.

In another embodiment, the present application provides a method for manufacturing a test strip. The method comprises: providing a sheet-shaped article which is composed of a plurality of test strips, wherein each of the test strips comprises a base layer, an intermediate layer, a blood retaining layer, an upper layer, and a reagent, the blood retaining layer comprises a slit and a blood retaining region fluidly commuted with the slit, and the reagent is disposed on a surface of the intermediate layer and exposed in the slit; providing a predetermined depth from an interface between the slit and the upper layer to an upper surface of the reagent for the test strips; measuring an actual depth from the interface between the slit and the upper layer to the upper surface of the reagent for each of the test strips; performing calculation to respectively obtain a correction factor for each of the test strips according to the actual depth and the predetermined depth for each of the test strips; labeling corresponding one of classification marks on each of the test strips according to the correction factor associated with each of the test strips; and dividing the sheet-shaped article and cutting the test strips into each individual unit.

In another embodiment, the classification mark is labeled on the upper surface of the upper layer or the lower surface of the base layer of the test strip by a laser marker or an inkjet printer, wherein the classification mark is distinguished by different patterns or dot symbols with different gray levels for various groups.

BRIEF DESCRIPTION OF THE DRAWINGS

In order to sufficiently understand the essence, advantages and the preferred embodiments of the present invention, the following detailed description will be more clearly understood by referring to the accompanying drawings.

DETAILED DESCRIPTION OF THE INVENTION

The following description shows the preferred embodiments of the present invention. The present invention is described below by referring to the embodiments and the figures. Thus, the present invention is not intended to be limited to the embodiments shown, but is to be accorded the principles disclosed herein. Furthermore, that various modifications or changes in light thereof will be suggested to persons skilled in the art and are to be included within the spirit and purview of this application and scope of the appended claims.

Figure 3:
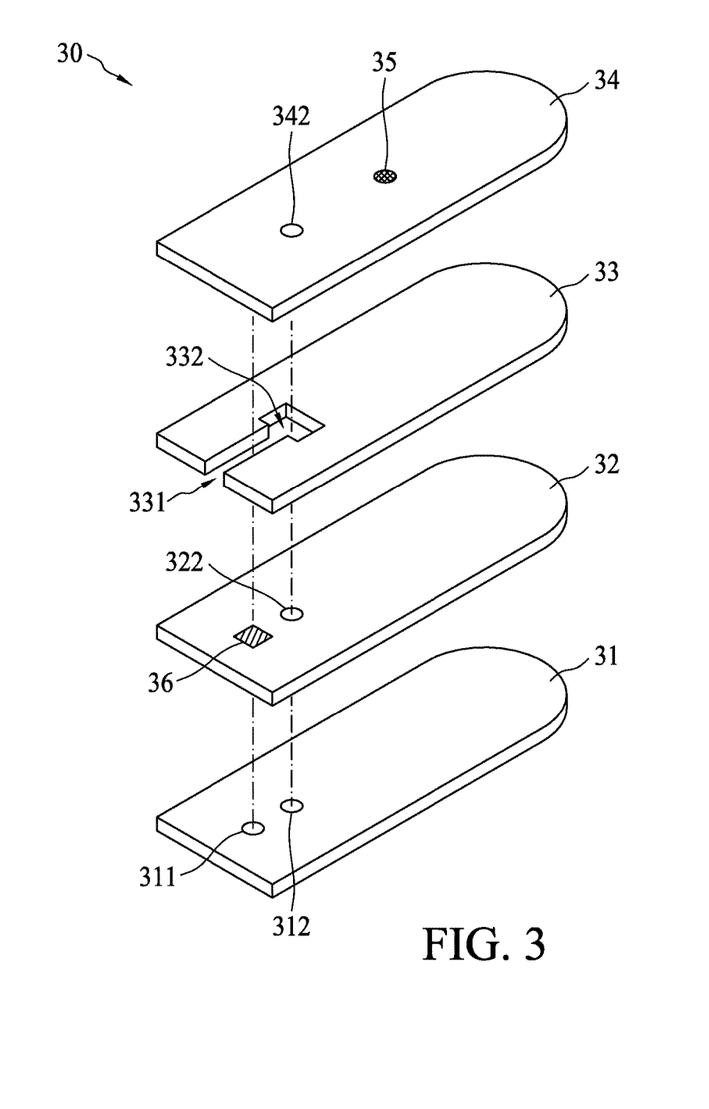
FIG. 3 is a perspective exploded schematic diagram illustrating a test strip of this application in accordance with an embodiment of the present application.

FIG. 3 is a perspective exploded schematic diagram illustrating a test strip of this application in accordance with an embodiment of the present application. The test strip 30 comprises a base layer 31, an intermediate layer 32, a blood retaining layer 33 and an upper layer 34. The upper layer 34 is a transparent film layer formed by an adhesive material. The upper surface of the top layer 34 is marked with a classification mark 35 to distinguish the characteristics and classification of the test strip 30. In this embodiment, the classification mark 35 is used to distinguish the groups representative of the variation (further discussed in the following paragraphs and FIG. 4) in the actual depth from the interface between the slit 311 of the blood retaining layer 33 and the upper layer 34 to the upper surface of the reagent 36. The classification mark is marked on such as, but not limit to, the upper surface of the top layer 34 and the lower surface of the base layer 31 so that an optical blood glucose detection device or optical blood glucose meter can identify the classification mark and then correct the blood glucose value. In this embodiment, the classification mark 35 may be marked or labeled by a laser machine or an inkjet printer. For example, a pattern, dot mark or dot symbol with different gray levels is labeled by a laser machine. In the next embodiment, the classification mark 35 is marked by a laser machine with patterns (a, b, c, d, e, f, g, h, i, j, k), dot marks or dot symbols with different gray levels (for example, gray scales 1-11) (as described in the following paragraphs and Table 1 below).

TABLE 1

| Actual Depth | Correction Factor | Classification Mark |
|---|---|---|
| 55 μm | −10% | Pattern a |
| 54 μm | −8% | Pattern b |
| 53 μm | −6% | Pattern c |
| 52 μm | −4% | Pattern d |
| 51 μm | −2% | Pattern e |
| 50 μm | 0 | Pattern f |
| 49 μm | +2% | Pattern g |
| 48 μm | +4% | Pattern h |
| 47 μm | +6% | Pattern i |
| 46 μm | +8% | Pattern j |
| 45 μm | +10% | Pattern k |

The base layer 31 of the test strip 30 can be made of opaque plastic materials, such as a black polyethylene terephthalate (PET) film layer, which includes an opening 311 and a through hole 312. The intermediate layer 32 is a transparent film layer, and includes a through hole 322 aligned with the through hole 312. The predetermined thickness of the blood retaining layer 33 is preferably 54 μm. The blood retaining layer 33 has a slit 331 extending from the outside to the inside. The blood sampled from the finger of the subject can be introduced into the inside of the blood retaining region 332 through the slit 331. The upper layer 34 can be made of a transparent plastic material, such as a transparent polyethylene terephthalate film layer, and includes a through hole 342. In particular, the intermediate layer 32 is attached with a reagent 36 which is close to the surface of the blood retaining layer 33. The reagent 36 is exposed in the slit 331 and aligned with the opening 311 of the base layer 31. Light will penetrate the transparent upper layer 34 and the intermediate layer 32 and pass through the reagent 36 and exit from the opening 311. In this embodiment, the base layer 31, the intermediate layer 32, and the upper layer 34 may be the same thickness film layer, and the blood retaining layer 33 has a thickness smaller than the other layers. In addition, the base layer 31 is a plastic film layer formed of a single-sided adhesive material, and the blood retaining layer 33 is a transparent film layer formed of an adhesive material. However, because the adhesive material of the blood retaining layer 33 or the reagent 36 on the intermediate layer 32 is coated unevenly or contracted, it is difficult to control the uniformity of the optical path length in the slit 331 (i.e., the predetermined depth described later). The classification mark 35 is used to distinguish the corrections (or compensations) for different groups representative of the variation (i.e., the difference between the actual depth and the predetermined depth) in the actual depth from the interface between the slit 311 of the blood retaining layer 33 and the upper layer 34 to an upper surface of the reagent 36.

In addition, the centers of the through holes 312, 322, and 342 of the other group are also aligned with each other, and their center lines pass through the blood retaining region 332. That is, they communicate with each other. Similarly, the volume percentage (i.e., the hemolysis ratio; HCT) of the red blood cells (RBC) in the blood is obtained to redefine a measured blood glucose value by optical measurement. Because the measured blood glucose value is often affected by the hemolysis ratio, the measured hemolysis ratio can be used to correct the measured blood glucose value. The measurement of the hemolysis ratio is not the focus of the present application, so it will not be further discussed hereinafter.

Figure 4:
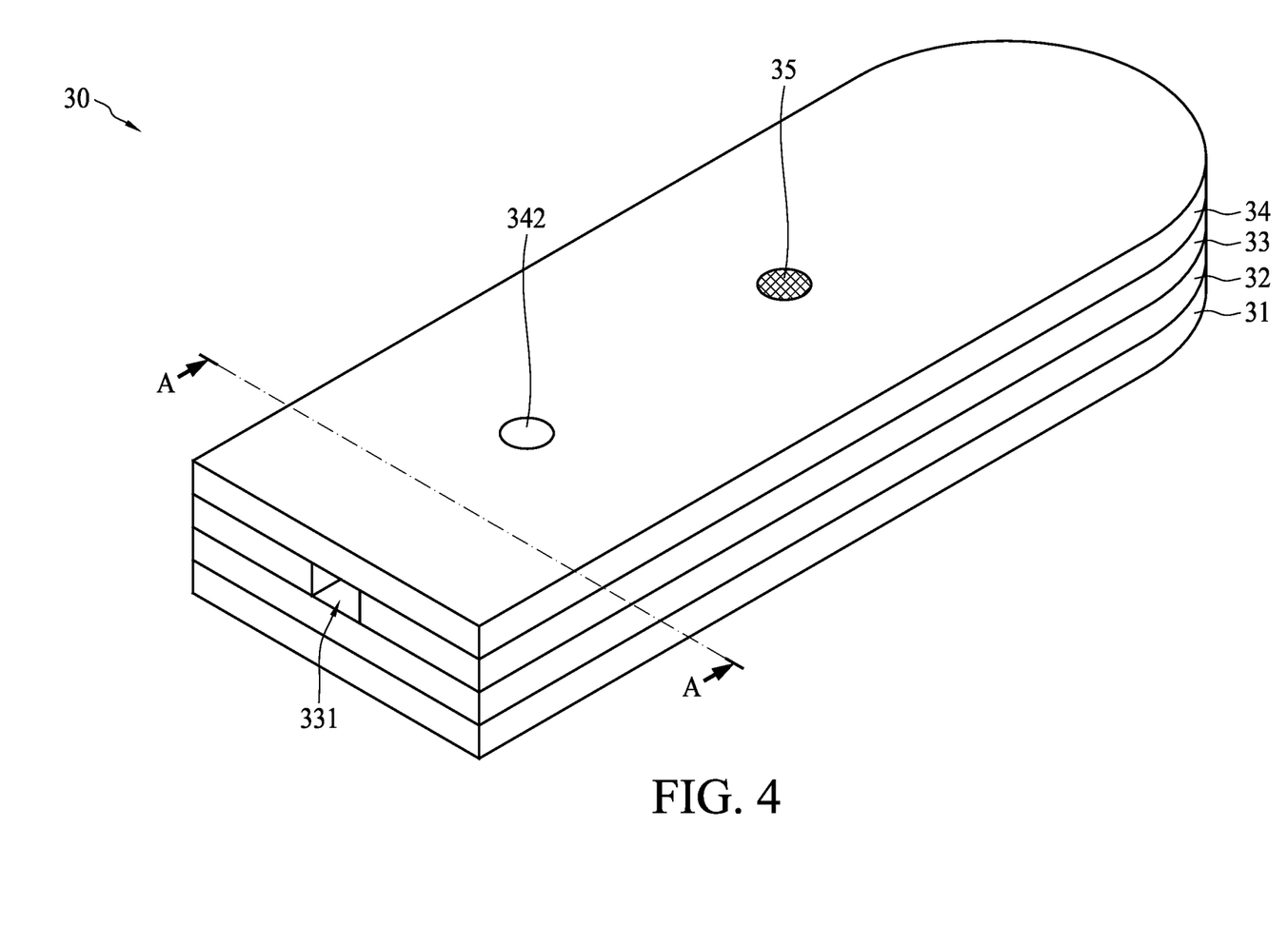
FIG. 4 is a perspective schematic diagram illustrating a test strip of this application in accordance with an embodiment of the present application.

FIG. 4 is a perspective schematic diagram illustrating a test strip of this application in accordance with an embodiment of the present application. A blood sampling needle (not shown in the figure) is used to take a blood sample from the subject's finger, and the blood will be introduced into the inside of the blood retaining region 332 through the slit 331, and react with the reagent 36. The concentration of the reaction product is positive proportional to the blood glucose value, or they have a proportional relationship. Accordingly, a color change occurs in the blood so that the blood glucose value can be obtained by colorimetric analysis. It is specifically stated here that the result of the colorimetric analysis is positive proportional to the blood glucose value.

Colorimetry is a quite well-known method used in the biochemical testing field. It uses the Beer-Lambert Law as the basis for calculating the concentration of reaction products. The calculation formula is expressed as:

$$A = \alpha L C \quad \text{(Formula 1)}$$

A is the absorptivity for light; $\alpha$ is an absorption coefficient; L is the optical path length or the thickness of the absorption layer; C is the concentration of the light-absorbing substance.

Figure 5:
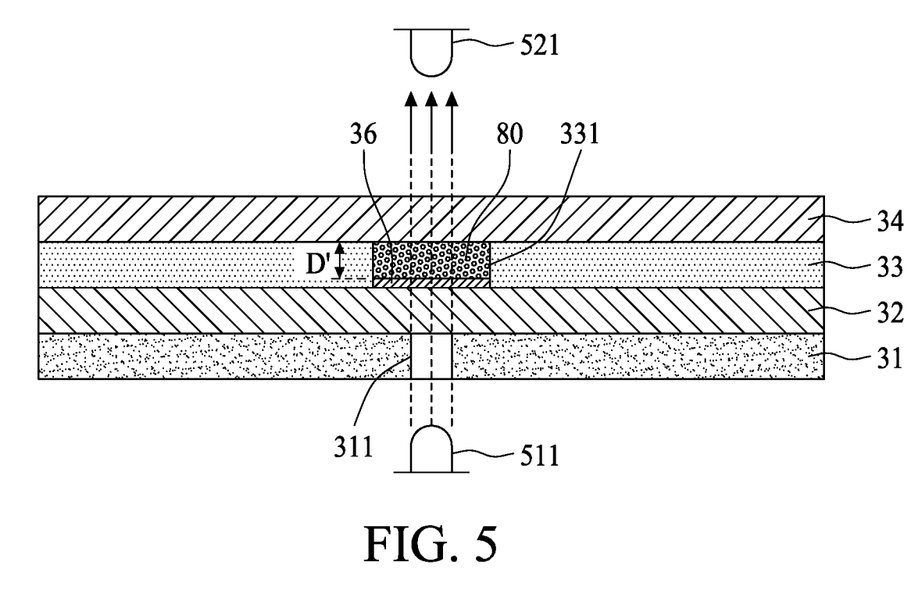
FIG. 5 is a schematic diagram illustrating the test strip taken along the A □ A cross-sectional line in FIG. 4 and the optical inspection used thereof.

FIG. 5 is a schematic diagram illustrating the test strip along the A□A cross-sectional line in FIG. 3 and the optical inspection used thereof. The light-emitting device 511 (e.g. a light-emitting diode) is aligned with the opening 311 of the base layer 31 to emit light. The light first passes through the opening 311 and the transparent intermediate layer 32, and a part of the light is absorbed by the blood 80 that has reacted with the reagent 36. The other part of light will penetrate the blood 80 and reach the light receiving device 521 (e.g. a photodiode) through the upper layer 34. Theoretically, the thickness of the blood retaining region 332 minus the thickness of the reagent 36 is the optical path length of the foregoing Formula 1. If the test strip 30 is designed in a manner that the predetermined thickness of the blood retaining region 332 is 54 µm and the predetermined thickness of the reagent 36 is 4 µm, it is necessary to keep the optical path length (i.e. the predetermined depth in the slit 331) at exact 50 µm (ideal design value) in order to make the colorimetric analysis result be acceptable or within an allowable error range, otherwise the deviation of a measured concentration value will exceed an allowable tolerance. However, during an actual manufacturing process, the blood retaining layer 33 is connected with the top layer 34 and the intermediate layer 32 by an adhesive material. It is difficult to keep the actual depth D' in the slit 331 uniform and even equal to a predetermined depth (D, not shown in the figure) since the reagent 36 is coated unevenly or the upper and lower layers are shrunk or compressed during the manufacturing process of test strips. These troublesome issues severely affect the optical path length L in the Formula 1.

However, the preferred embodiment of the present application sets the optical path length L to be a constant predetermined depth, i.e., 50 µm, but the present application is not limited to this value. In other embodiments, the predetermined depth may vary according to actual design requirements. For example, the predetermined depth may be between 40 µm and 50 µm. During the practical manufacturing process, first, the actual depth D' in the slit 331 for each of the plural test strips 30 can be swiftly measured through an optical measuring instrument (e.g. optically measuring the thickness of a film). Moreover, a correction factor is set to be the product of a difference between the predetermined depth D and the actual depth D' and a reciprocal (about 2%) of the predetermined depth. Afterward, the correction factors corresponding to the plurality of test strips are marked using the classification marks 35 with different gray levels so that the test strips pertain to various groups. In short, the foregoing classification mark 35 can be used to distinguish the different groups representative of the variation of the actual depth in the slit 331 of the blood retaining layer 33 so that the error caused by the variation of the optical path length in Formula 1 can be corrected. For example, if the measured actual depth D' is 54 µm, the value calculated by Formula 1 needs to be compensated by approximately (50−54)×2%, which is minus 8%. By contrast, if the actual thickness D' is 47 µm, the value calculated by Formula 1 needs to be compensated by about (50−47)×2%. That is, because the actual depth (the actual optical path length) is less than the predetermined depth, the measured blood glucose value is compensated by 6%. Therefore, 1.06 times the measured blood glucose value is the final displayed blood glucose value.

Figure 6:
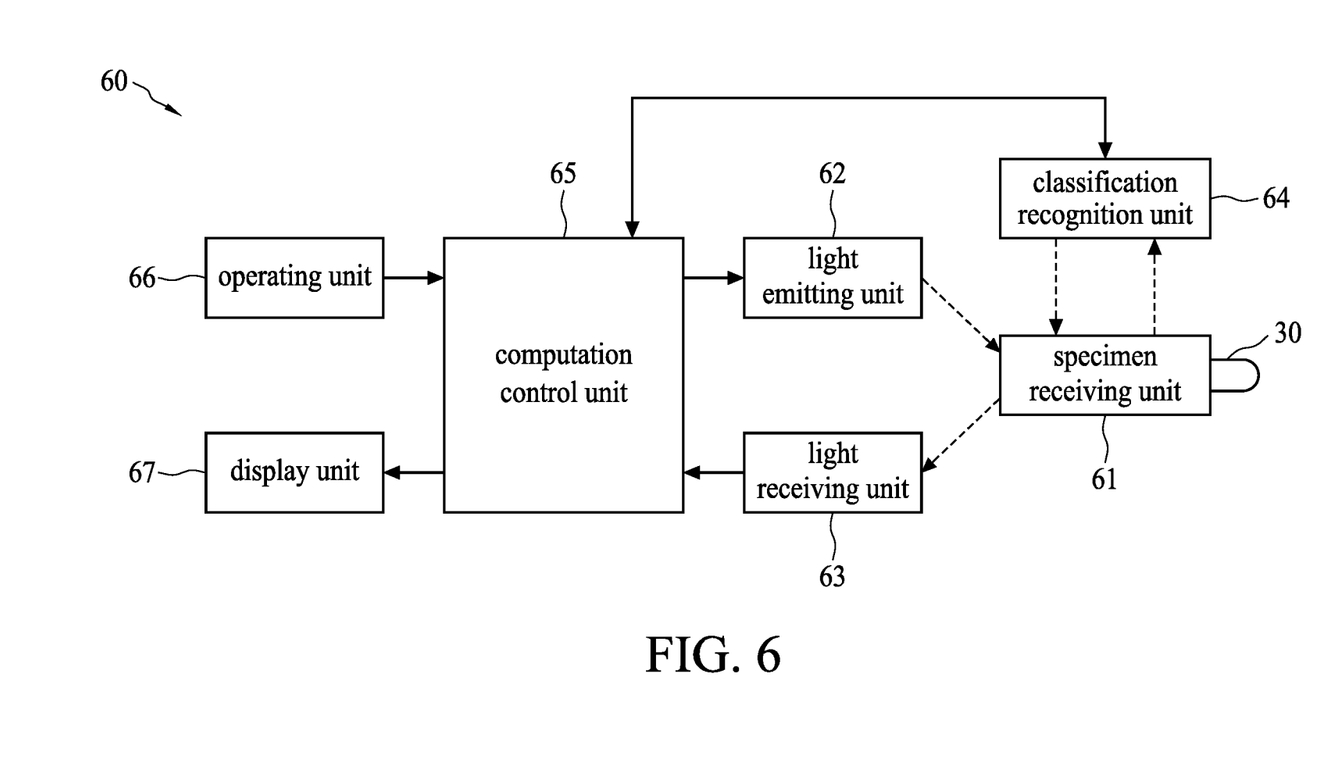
FIG. 6 is a block diagram illustrating an optical blood glucose detection device in accordance with an embodiment of the present application.

FIG. 6 is a block diagram illustrating an optical blood glucose detection device in accordance with an embodiment of the present application. As shown in the figure, an optical blood glucose detection device 60 is used to measure the blood glucose value of blood stored in the test strip. The device 60 includes a specimen receiving unit 61, a light emitting unit 62, a light receiving unit 63, a classification recognition unit 64, and a computation control unit 65. The specimen receiving unit 61 accommodates the test strip 30. The light emitting unit 62 emits light toward the test strip 30, and may include the light emitting device 511 as shown in FIG. 5. The light receiving unit 63 detects light passing through the blood, and may include the light receiving device 521 as shown in FIG. 5. The classification recognition unit 64 reads the classification mark 35 on the test strip 30, which may also include a light-emitting device for projecting light and a light-receiving element for sensing reflected light (not shown). The computation control unit 65 performs the foregoing colorimetric analysis based on the signal generated by the light receiving unit 63, and compensates for the variation in the actual depth of the slit 331 of the blood retaining layer 33 in the test strip 30 according to the correction factor generated by the classification recognition unit 64, which causes the error of the colorimetric analysis. The optical blood glucose detection device 60 further includes an operating unit 66 that can be touched and set by the user, and a display unit 67 that can display the setting value and the measurement result.

Figure 7:
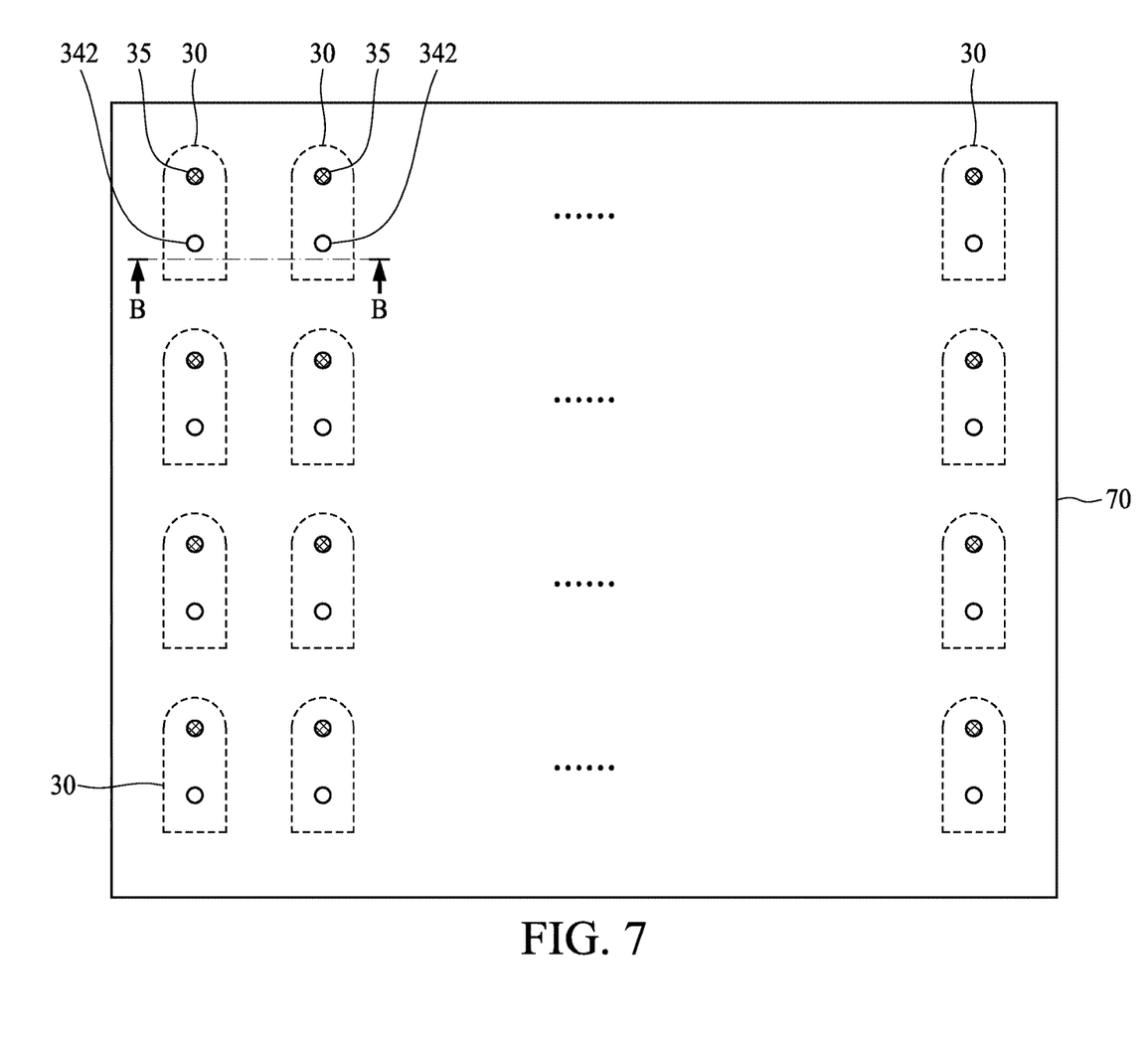
FIG. 7 is a schematic diagram illustrating a plurality of test strips during a manufacturing process in accordance with an embodiment of the present application.

FIG. 7 is a schematic diagram illustrating a plurality of test strips during a manufacturing process in accordance with an embodiment of the present application. In the process of mass-produced test strips, the undivided base layers 31, middle layers 32, blood storage layers 33, and top layers 34 respectively with large areas are sequentially stacked or coated together to form a sheet-shaped article including a plurality of test strips 30 to be subsequently cut. After the stacking of the sheet-shaped article 70 is completed, an actual depth is measured from an interface between the slit 331 and the upper layer 34 to an upper surface of the reagent 36, and then a correction factor is calculated according to the predetermined depth. Afterward, according to the correction factor, the corresponding classification mark 35 is sequentially marked on each test strip 30. In this embodiment, the calculation equation of the correction factor is the difference between the predetermined depth and the actual depth multiplied by the reciprocal of the predetermined depth.

Figure 8:
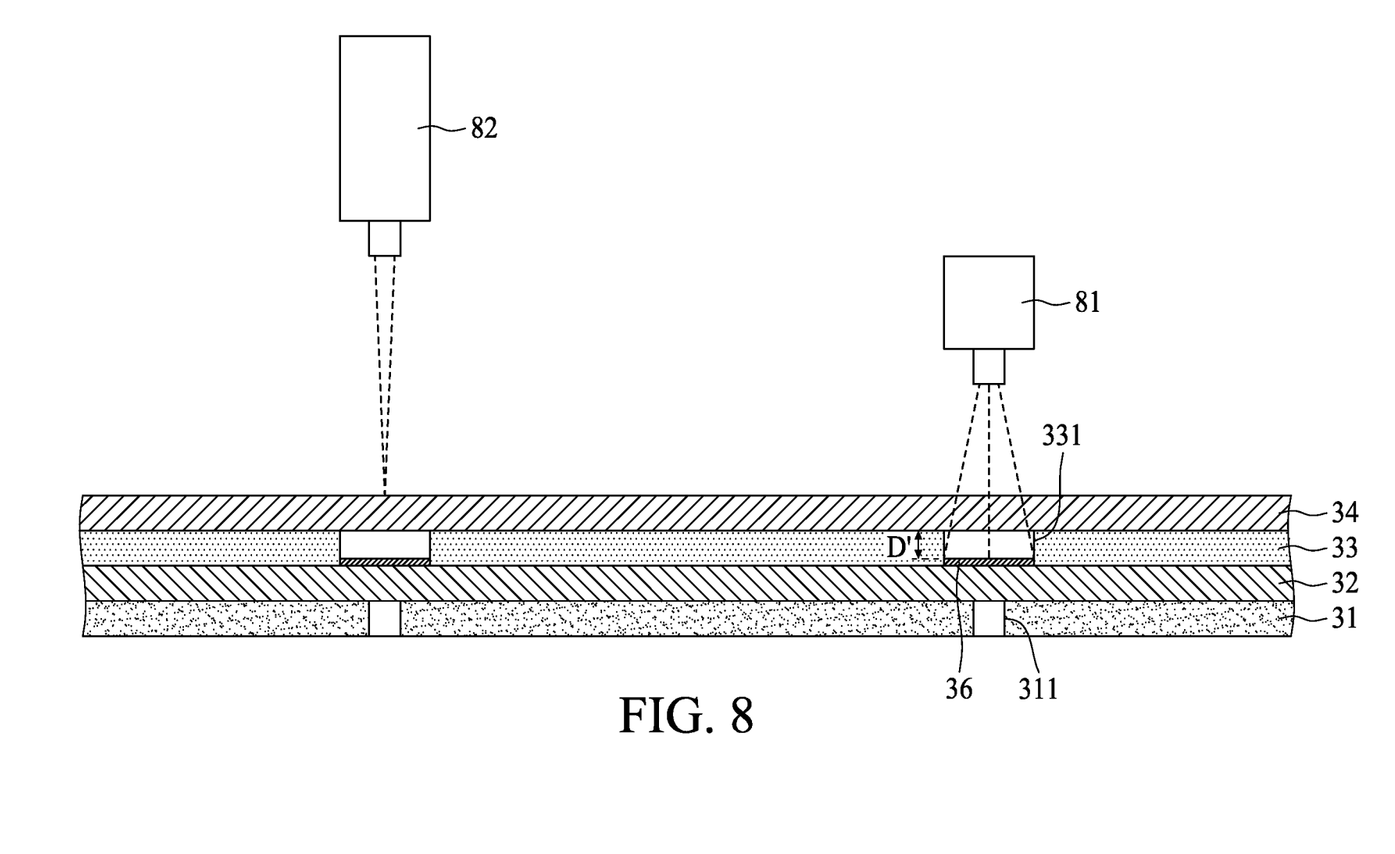
FIG. 8 is a schematic diagram illustrating the measurement of actual depths and the labeling of classification marks during a manufacturing process in accordance with an embodiment of the present application.

FIG. 8 is a cross-sectional diagram taken along the B □ B cross-sectional line in FIG. 7. In detail, FIG. 8 is a schematic diagram illustrating the measurement of actual depths and the labeling of classification marks during a manufacturing process in accordance with an embodiment of the present application. In this embodiment, an optical measuring instrument 81, such as a film thickness meter, is used to quickly measure the actual depth D' from the interface between the slit 331 and the upper layer 33 to the upper surface of the reagent 36 for each test strip 30 along an S-like path. The optical measuring instrument 81 can emit light of a specific wavelength, and then according to the light reflected by the upper surface of the reagent 36 and/or the intermediate between the slit 331 and the upper layer 33, analyze them to have the actual depth D'. The embodiment only exemplifies that the optical measuring instrument for measuring the actual depth D' is a film thickness meter, but the invention is not limited to this. The actual depth D' of each test strip 30 is substituted into the calculation equation of the foregoing correction factor so that the corresponding correction factor of each test strip 30 can be obtained. In view of a corresponding relationship or correspondence table (See Table 1 above) between the correction factor and the classification mark, a laser marker 82 or an inkjet printer is used to generate the symbol of the classification mark 35 or mark it on the upper surface of the upper layer 34 or the lower surface of the base layer 31.

However, the embodiment of the present invention only illustrates that the optical path length L is kept at a constant predetermined depth, i.e. 50 μm. In this embodiment, the predetermined depth may preferably be between 40 μm and 50 μm. The foregoing classification mark 35 can be used to distinguish the groups representative of the variation in the actual depth in the slit 311 of the blood retaining layer 33 so that the error caused by the variation of the optical path length in Formula 1 can be corrected, and further the measured blood glucose value can be directly compensated. For example, if the measured actual depth D' is 54 μm, the value calculated by Formula 1 needs to be compensated by approximately (50−54)×2%, which is minus 8%. Therefore, 0.92 times the measured blood glucose value is the final displayed blood glucose value. By contrast, if the actual thickness D is 47 μm, the value calculated by Formula 1 needs to be compensated by about (50−47)×2%. That is, because the actual depth (the actual optical path length) is less than the predetermined depth, the measured blood glucose value is compensated by 6%. Therefore, 1.06 times the measured blood glucose value is the final displayed blood glucose value.

Figure 9:
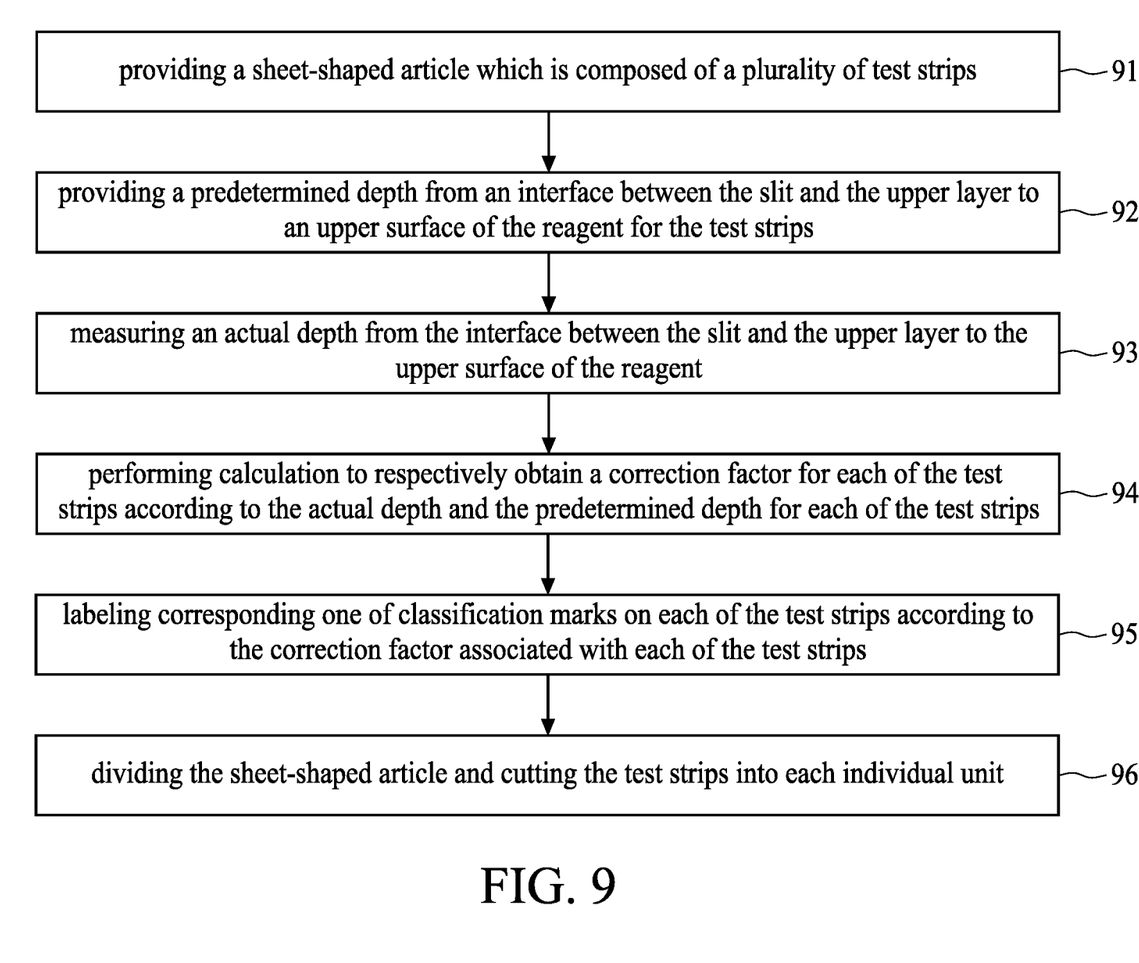
FIG. 9 is a flow chart illustrating the manufacture of test strips in accordance with an embodiment of the present application.

FIG. 9 is a flow chart illustrating the manufacture of test strips in accordance with an embodiment of the present application. In Step 91, a sheet-shaped article is provided, and is composed of a plurality of test strips, that is, the sheet-shaped article 70 as shown in FIG. 7. Then, a predetermined depth from an interface between the slit and the upper layer to an upper surface of the reagent for the test strips is provided, as shown in Step 92. Afterward, Step 93 is performed to measure an actual depth from the interface between the slit and the upper layer to the upper surface of the intermediate layer for each test strip. Next, the calculation is performed according to the actual depth and the predetermined depth of each test strip to obtain the correction factor of each test strip, as shown in Step 94. Step 95 is further executed to label the corresponding classification mark of each test strip according to the correction factor of each test strip. Finally, the sheet-shaped article 70 is divided and the test strips is cut into each individual unit, that is, the sheet-shaped article 70 is divided into a plurality of independent test strips 30 (as shown in FIG. 4), as shown in Step 96. In other embodiments, Steps 94 and 95 can be omitted or replaced. After Step 93, as shown in Table 1, a corresponding correction factor is found for each test strip by checking the actual depth of each test strip, and then the marking of patterns is performed. For example, if the actual depth of the test strip of the sheet-shaped article 70 is 54 μm, the correction factor table shows that the correction factor is minus 8%, and the pattern b can be marked on the test strip.

The foregoing embodiments of the invention have been presented for the purpose of illustration. Although the invention has been described by certain preceding examples, it is not to be construed as being limited by them. They are not intended to be exhaustive, or to limit the scope of the invention. Modifications, improvements and variations within the scope of the invention are possible in light of this disclosure.

What is claimed is:

1. A test strip, comprising:
a base layer;
an intermediate layer overlaid on the base layer;
a blood retaining layer comprising a slit and a blood retaining region fluidly commuted with the slit and overlaid on the intermediate layer;
an upper layer overlaid on the blood retaining layer;
a reagent disposed on a surface of the intermediate layer and exposed in the slit, wherein there are a predetermined depth and a actual depth from an interface between the slit and the upper layer to an upper surface of the reagent; and
a classification mark representing a correction factor and disposed on an upper surface of the upper layer or a lower surface of the base layer;
wherein the correction factor is the product of a difference between the predetermined depth and the actual depth and a reciprocal of the predetermined depth.

2. The test strip according to claim 1, wherein the base layer comprises an opening, and the opening is aligned with reagent.

3. The test strip according to claim 1, wherein the predetermined depth is between 40 μm and 50 μm.

4. The test strip according to claim 1, wherein each of the base layer, the intermediate layer, and the upper layer respectively comprises a through hole, and the three through holes are aligned with the blood retaining region.

5. The test strip according to claim 1, wherein the base layer is a black polyethylene terephthalate film layer.

6. The test strip according to claim 1, wherein the intermediate layer is a transparent film layer.

7. The test strip according to claim 1, wherein the blood retaining layer is a transparent film layer formed of an adhesive material.

8. The test strip according to claim 1, wherein the upper layer is a transparent polyethylene terephthalate film layer.

9. The test strip according to claim 1, wherein a thickness of the blood retaining layer is 54 µm.

10. A method for manufacturing a test strip, comprising:
providing a sheet-shaped article which is composed of a plurality of test strips, wherein each of the test strips comprises a base layer, an intermediate layer, a blood retaining layer, an upper layer, and a reagent, the blood retaining layer comprises a slit and a blood retaining region fluidly commuted with the slit, and the reagent is disposed on a surface of the intermediate layer and exposed in the slit;
providing a predetermined depth from an interface between the slit and the upper layer to an upper surface of the reagent for the test strips;
measuring an actual depth from the interface between the slit and the upper layer to the upper surface of the reagent for each of the test strips;
performing calculation to respectively obtain a correction factor for each of the test strips according to the actual depth and the predetermined depth for each of the test strips;
labeling a corresponding one of a plurality of classification marks on each of the test strips according to the correction factor associated with each of the test strips; and
dividing the sheet-shaped article and cutting the test strips into each individual unit;
wherein the correction factor is the product of a difference between the predetermined depth and the actual depth and a reciprocal of the predetermined depth.

11. The method for manufacturing a test strip according to claim 10, wherein the actual depth is measured by an optical measuring instrument.

12. The method for manufacturing a test strip according to claim 11, wherein the optical measuring instrument measure the actual depth for each test strip along an S-like path.

13. The method for manufacturing a test strip according to claim 10, wherein the corresponding one of the plurality of classification mark is labeled on the upper surface of the upper layer by a laser marker or an inkjet printer.

14. The method for manufacturing a test strip according to claim 10, wherein the corresponding one of the plurality of classification mark is labeled on the lower surface of the base layer by a laser marker or an inkjet printer.

15. The method for manufacturing a test strip according to claim 10, wherein the corresponding one of the plurality of classification mark is distinguished by different patterns with different gray levels for various groups.

16. The method for manufacturing a test strip according to claim 10, wherein the corresponding one of the plurality of classification mark is distinguished by different dot symbols with different gray levels for various groups.

17. The method for manufacturing a test strip according to claim 10, wherein the corresponding one of the plurality of classification mark is used to correct an error resulted from a difference between the predetermined depth and the actual depth in a colorimetric analysis.

18. The method for manufacturing a test strip according to claim 17, wherein the colorimetric analysis calculates a concentration of a reaction product between blood and the reagent based on a formula of Beer-Lambert Law.

19. The method for manufacturing a test strip according to claim 18, wherein the difference between predetermined depth and the actual depth causes a variation in an optical path length of the formula of Beer-Lambert Law.

20. The method for manufacturing a test strip according to claim 19, wherein the corresponding one of the plurality of classification mark is used to correct an error of the calculated concentration of the reaction product caused from the variation.

\* \* \* \* \*